United States Patent [19]

Shih et al.

[11] Patent Number: 5,139,770
[45] Date of Patent: * Aug. 18, 1992

[54] COSMETIC COMPOSITIONS CONTAINING STRONGLY SWELLABLE, MODERATELY CROSSLINKED POLYVINYLPYRROLIDONE

[75] Inventors: Jenn S. Shih, Paramus; Jui-Chang Chuang, Wayne; Terry E. Smith, Morristown; Carmen D. Bires, Hackettstown; Michael W. Helioff, Westfield; Robert B. Login, Oakland, all of N.J.

[73] Assignee: ISP Investments Inc., Wilmington, Del.

[*] Notice: The portion of the term of this patent subsequent to Dec. 17, 2008 has been disclaimed.

[21] Appl. No.: 628,122

[22] Filed: Dec. 17, 1990

[51] Int. Cl.⁵ .................. A61K 31/79; A61K 7/06; A61K 7/16; A61K 7/42
[52] U.S. Cl. .................. 424/59; 424/401; 424/489; 424/70; 424/71; 424/73; 514/847; 514/881; 526/258; 526/264
[58] Field of Search .................. 424/401, 489, 59, 70, 424/71, 73, 80; 514/847, 881; 526/258, 264

[56] References Cited

U.S. PATENT DOCUMENTS 4,719,099  1/1988  Grollier et al. ............. 424/70

Primary Examiner—Allen J. Robinson
Assistant Examiner—Brian Bembenick
Attorney, Agent, or Firm—Walter Katz; Marilyn J. Maue; Joshua J. Ward

[57] ABSTRACT

What is provided herein are cosmetic compositions for the care of hair and skin containing about 0.2 to 10% by wt. of a strongly swellable, moderately crosslinked polyvinylpyrrolidone polymers in the form of fine, white powders characterized by (a) an aqueous swelling parameter defined by its gel volume of about 15 to 150 ml/g, (b) a Brookfield viscosity in 5% aqueous solution of at least about 10,000 cps, and (c) being prepared directly by a precipitation polymerization process in an organic solvent, in the presence of about 0.2 to 1% by weight of vinylpyrrolidone of a multifunctional crosslinking agent, preferably about 0.25 to 0.6%, and optimally, about 0.35 to 0.6%.

8 Claims, No Drawings

COSMETIC COMPOSITIONS CONTAINING STRONGLY SWELLABLE, MODERATELY CROSSLINKED POLYVINYLPYRROLIDONE

BACKGROUND OF THE INVENTION

1. Field of the Invention

This invention relates to cosmetic compositions, and more particularly, to personal care compositions for treating hair and skin which contains strongly swellable, moderately crosslinked polyvinylpyrrolidone (PVP) polymers.

2. Description of the Prior Art

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, amine lauryl sulfates and sodium lauryl sulfate ethers which have been found to be incompatible with most cationic conditioning agents at effective concentration levels.

Additionally, reproducible thickening for formulations containing anionic detergents such as sodium α-olefin sulfonates is very difficult to achieve.

Accordingly, it is an object of this invention to minimize or obviate the above problems while providing additional benefits in hair and skin treating formulations.

Another object of the invention is to provide cosmetic compositions containing strongly swellable, moderately crosslinked polyvinylpyrrolidone polymers which have excellent hair conditioning and thickening properties when incorporated into a shampoo and having high compatibility with components of hair and skin treating formulations.

Among the other objects herein is to provide a sunscreen lotion which is water-resistant.

These and other objects and features of the invention will be made apparent from the following description which follows.

SUMMARY OF THE INVENTION

What is provided herein are cosmetic compositions containing about 0.2 to 10% by wt. of a strongly swellable, moderately crosslinked PVP polymers in the form of fine, white powders having (a) an aqueous gel volume of about 15 to 150 ml/g of polymer, (b) a Brookfield viscosity in 5% aqueous solution of at least about 10,000 cps, which (c) are prepared directly by precipitation polymerization of vinylpyrrolidone (VP) in the presence of a crosslinking agent in the amount of about 0.2 to 1% by weight of VP. Preferably (a) is 25 to 75 ml/g of polymer, (b) is at least 15,000 cps, and (c) is about 0.25 to 0.8%, and, most preferably, (a) is 30 to 60 ml/g, (b) is about 20,000 to 50,000 cps, and (c) is about 0.35 to 0.6%.

The cosmetic compositions of the invention are used particularly for the personal care of hair and skin, typically conditioning shampoos, lotions for the treatment of hand and body, and sunscreen formulations which are water-resistant.

DETAILED DESCRIPTION OF THE INVENTION

In accordance with the invention, strongly swellable, moderately crosslinked PVP polymers are prepared directly in the form of fine, white powders by precipitation polymerization of vinylpyrrolidone in the presence of a predetermined amount of a crosslinking agent and free radical polymerization initiator in an organic solvent, preferably an aliphatic hydrocarbon, e.g. a $C_3$–$C_{10}$ saturated, branched or unbranched, cyclic or acyclic aliphatic hydrocarbon, and most preferably cyclohexane or heptane, or mixtures thereof.

The amount of solvent used in the process of the invention should be sufficient to dissolve an appreciable amount of the reactants and to maintain the copolymer precipitate in a stirrable state at the end of the polymerization. Generally, about 10 to 50% solids, preferably 15–30%, is maintained in the reaction mixture.

The precipitation polymerization process of the invention is carried out in the presence of a suitable free radical polymerization initiator. Suitable initiators include acyl peroxides such as diacetyl peroxide, dibenzoyl peroxide and dilauryl peroxide; peresters such as t-butylperoxy pivalate, tert-butyl peroxy-2-ethylhexanoate; peroxides such as di-tert-butyl peroxide; percarbonates such as dicyclohexyl peroxydicarbonate; and azo compounds such as 2,2'-azobis(isobutyronitrile), 2,2'-azobis(2,4-dimethylvaleronitrile), 1,1'-azobis(cyanocyclohexane), and 2,2'-azobis(methylbutyronitrile). Other initiators known in the art also may be used. A preferred initiator is the following:

| Preferred Initiator | | |
| --- | --- | --- |
| t-Butyl peroxypivalate | Atochem N.A. (Lupersol 11) | Liquid; 75% active in mineral spirits |

The amount of such initiator may vary widely; generally about 0.2–5.0% is used, based on the weight of total monomers charged.

The reaction temperature may vary widely; generally the reaction mixture is maintained at about 40°–150° C., preferably 60°–70° C., during the polymerization. Pressure usually is kept at atmospheric pressure, although higher and lower pressures may be used as well.

The reaction mixture should be stirred vigorously under an inert atmosphere, e.g. nitrogen, during the polymerization. A stirring rate of about 100–600 rpm in a 1-liter lab reactor is quite adequate to effect the desired polymerization and to keep the precipitate in a stirrable state during the polymerization.

Suitable crosslinking agents for use in the invention include such multifunctional compounds as the divinyl ethers of an aliphatic diol, e.g. the divinyl ethers of 1,3-propanediol, 1,4-butanediol, 1,5-pentanediol, 1,6-hexanediol, 1,7-heptanediol, 1,8-octanediol, 1,9-nonanediol, 1,10-decanediol, 1,11-unidecanediol, and 1,12-dodecanediol; as well as the divinyl ethers of diethylene glycol, triethylene glycol, tetraethylene glycol, pentaethylene glycol, hexaethylene glycol, heptaethylene glycol, octaethylene glycol, nonaethylene glycol, decaethylene glycol and further polyalkylene glycols up to a molecular weight of about 6000. Other suitable crosslinking agents include 1,7-octadiene, 1,9-decadiene, 1,13-tetradecadiene, divinylbenzene, N-N'-divinylimidazolidone, and methylene bisacrylamide; acrylates such as polyethylene glycol diacrylate, trimethylolpropane triacrylate, propylene glycol diacrylate; allyl ether derivatives of polyhydric alcohols such as pentaerythritol triallyl ether; or polyhydric alcohols esterified once or twice with acrylic acid; triallylamine, tetraallylethylenediamine, diallyl phthalate, and the like. Preferred crosslinking agents are the following: N,N'-divinylimidazolidone, pentaerythritol triallyl ether, triallyl-1,3,5-triazine-2,4,6(1H,3H,5H)-trione and 2,4,6-triallyloxy-1,3,5-triazine.

The precipitation polymerization process of the invention may be carried out by first precharging a suitable reactor with a predetermined amount of the organic solvent, for example, an aliphatic hydrocarbon solvent, and heating the solvent to a desired reaction temperature while stirring vigorously under an inert gas atmosphere. The initiator is then charged into the reactor. Then a solution containing selected amounts of vinylpyrrolidone monomer and the crosslinker material is admitted into the reactor over a period of time, generally about an hour or more, and preferably below the surface of the solvent. Then the reaction mixture is held for an additional period of time for polymerization to be completed. Finally, the mixture is cooled to room temperature. Filtering, washing with solvent, and drying provides the desired polymer in yields approaching quantitative. Alternatively, the reaction product may be dried directly to provide the polymer powders.

The heterogeneous polymerization process of the invention in cyclohexane or heptane solvent provides the desired PVP polymer product as a fine, white powder, which precipitates readily, in quantitative yield, with substantially the same degree of crosslinking as the charge of VP monomer and crosslinking agent, in a smooth polymerization without excessive swelling of polymer during the course of the process. More particularly, the solvents of the invention are non-solvents for PVP and enable the polymerization to proceed in the presence of crosslinking agent without excessive building up viscosity of the reaction mixture during polymerization.

In summary, the fine, white powder polymers of the invention are prepared directly by a precipitation polymerization process in an organic solvent, such as an aliphatic hydrocarbon solvent, preferably cyclohexane or heptane, or an aromatic hydrocarbon, such as toluene, in the presence of about 0.2 to 1% by weight of VP of a crosslinking agent, preferably N,N'-divinylimidazolidone, triallyl-1,3,5-triazine-2,4,6(1H,3H,5H)-trione, 2,4,6-triallyloxy-1,3,5-triazine, and pentaerythritol triallyl ether at about 10 to 50% solids.

The present crosslinked polyvinylpyrrolidone polymers possess unique properties, among which is their ability to build viscosity, while simultaneously providing a hair and skin conditioning capability in cosmetic formulations containing anionic surfactants. These compounds are highly compatible with α-olefin sulfonates and anionic surfactant salts conventionally employed in shampoos and skin lotions. Their compatibility is such that up to 5% by weight or more of the polymer compounds can be incorporated in the formulation; a characteristic which permits the formation of effective formulations as liquids or gels, and can be employed in shampoos, hair conditioners and lotions as an agent which incorporates thickening and conditioning qualities in one additive; thus eliminating the need for separate chemical components to accomplish these individual needs. Generally, the compounds of this invention are mixed with a standard formulation of shampoo, cream rinse, hand or body lotion or creams, sunscreen, etc., in an effective amount which ranges from between about 0.2 to about 10% by weight, preferably between about 0.5 and about 5% by weight, of the total formulation. The present compounds in concentrations up to 5% by weight show no tendency to precipitate after extended periods including periods up to 6 months or more.

For incorporating into a standard formulation of shampoo, cream rinse, hand or body lotion, etc., the present product is dissolved in an inert solvent such as water, propylene glycol, ethanol, etc., and the solution in the desired amount is mixed into the formulation to provide a homogeneous liquid, gel, cream or lotion. Incorporation of the present product is usually affected at room temperature under atmospheric pressure and requires no special formulating technique. However, for certain formulations incorporation of the present product can be effected at temperatures up to about 85° C. Amphoteric-containing shampoo formulations are best prepared by initially preparing an aqueous solution of the polymer and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE 1

A 2-liter, 4-necked reaction vessel was equipped with a condenser, a constant speed mechanical stirrer, set at 170 rpm with a torque indicator and an anchor agitator having an open radius of 4 and 5/6 inches, an adaptor for admitting nitrogen, and a thermocouple connected to a temperature controller. The vessel was charged with 1000 g. of cyclohexane and heated to 65° C. during 30 minutes while purging with nitrogen. The reactor then was held at 65° C. for an additional 30 minutes. Then 520 microliters of t-butylperoxy pivalate (Lupersol 11, 75% active) polymerization indicator was added. Thereafter a solution of 250 g. of vinylpyrrolidone and 1.25 g. of N,N'-divinylimidazolidone crosslinking agent was introduced into the charged reactor over a period of 4 hours while stirring the contents. The feeding rate was about 1.0 ml./min. Then the mixture was heated to 85° C. over a half-hour and held at that temperature for another half-hour. Then the mixture was transferred to a 2-liter high pressure reactor and 1.0 g. of 2,5-dimethyl-2,6-di-(t-butylperoxy)hexane (Lupersol 101, 90% active) was added. The reactor was sealed and heated to 130° C. for 8 hours, cooled to room temperature, and the mixture was dried in a rotary evaporator. The polymer product was oven dried at 100° C. and vacuum dried at 90° C. for 16 hours of each. A quantitative yield of a crosslinked PVP polymer containing about 0.5% crosslinking agent was obtained.

EXAMPLES 2–10

The procedure of Example 1 was followed using various amounts of different crosslinkers with the following results.

TABLE I

| Ex. No. | VP, Amount (g) | Cross-linker* | Cross-linker, Amount (g) | % Cross-linker | Product Yield (%)** |
|---|---|---|---|---|---|
| 2 | 250 | DI | 0.25 | 0.10 | 96.0 |
| 3 | 250 | DI | 0.625 | 0.25 | 100.0 |
| 4 | 250 | DI | 2.5 | 1.00 | 100.0 |
| 5 | 250 | PTE | 0.25 | 0.10 | 93.0 |
| 6 | 250 | PTE | 0.625 | 0.25 | 92.0 |
| 7 | 250 | PTE | 2.5 | 1.00 | 94.2 |
| 8 | 250 | MBA | 0.625 | 0.25 | 87.0 |
| 9 | 250 | MBA | 1.25 | 0.50 | 96.0 |
| 10 | 250 | MBA | 2.5 | 1.00 | 100.0 |

*DI = N,N'-divinylimidazolidone, PTE = pentaerythritol triallyl ether and MBA = methylene bisacrylamide
**based upon VP used, by weight

EXAMPLES 11-12

The procedure of Example 1 was followed using heptane as solvent in place of cyclohexane. The feeding rate of the solution of vinylpyrrolidone in crosslinking agent was 0.50–0.55 ml./min. The results are shown in Table II below.

TABLE II

| Ex. No. | VP, Amount (g) | Crosslinker | Amount (g) | % Crosslinker | Product Yield (%) |
|---|---|---|---|---|---|
| 11 | 200 | DI | 1.0 | 0.50 | 95.6 |
| 12 | 250 | PTE | 1.25 | 0.50 | 91.5 |

DI - N,N'-Divinylimidazolidone
PTE - Pentaerythritol triallylether

EXAMPLE 13

The reactor of Example 1 was provided with the anchor agitator positioned in the middle of the reactor and extended to within 2 inches of the bottom of the reactor. Two dip tubes were connected to two metering pumps. The thus-equipped reactor then was charged with the solvent which filled the reactor to about 4 inches above the bottom of the dip tubes. In this procedure, the solution of VP and crosslinking agent was admitted into the reactor through the dip tubes to a position below the surface of the solvent. The effect of such subsurface feeding of monomer-crosslinker solution was to reduce build-up of viscosity of the polymer product during the polymerization, resulting in a smoother course for the process, particularly with respect to effective stirring of the reaction mixture.

Properties of Polymer of Invention

The strongly swellable, moderately crosslinked PVP polymer powders of the invention are characterized by its unique gel volume and viscosity, which properties enable the polymer to thicken aqueous and non-aqueous solutions effectively.

Gel volume is a measure of the swelling property of the crosslinked polymer and is defined as the equilibrium aqueous swelling volume of polymer per unit weight, and is expressed in the units of ml/g. Gel volume is determined by first adding 1 g. of the polymer to a suitable graduated cylinder filled with water. This mixture then is shaken and allowed to stand at room temperature for 3 days. The volume of the gel which is produced in water is measured and taken as the gel volume. Similarly, the gel volume concept can be applied to non-aqueous systems.

The viscosity of the polymer is defined by its Brookfield viscosity in cps, which is determined upon a 5% aqueous solution of the polymer at 25° C. by a standard analytical procedure using Model LTV and Spindle No. 4.

For maximum utility, it is desirable that the hydrated polymer exhibit a high gel volume and a high viscosity. With increasing crosslinking density in the polymer, the gel volume decreases and viscosity increases and then decreases, passing through a maximum. In the crosslinked polymer system of this invention, an effective thickener product is provided by including crosslinker in the reaction mixture at a suitable concentration of about 0.2 to 1.0 % by weight, based upon VP, preferably about 0.25 to 0.8%, and optimally, at about 0.35 to 0.6%. At this suitable amount of crosslinker loading, the crosslinked polymer product exhibits a gel volume of about 15 to 150 ml/g of polymer and a Brookfield viscosity of at least 10,000 cps. At the preferred crosslinker concentration, the gel volume is about 25 to 75 ml/g of polymer and its Brookfield viscosity is at least 15,000 cps. At the optimal amount crosslinker present in the reaction mixture, the polymer exhibits a gel volume of about 30 to 60 ml/g of polymer and a Brookfield viscosity of about 20,000 to 50,000 cps.

The viscosity of the crosslinked polymer of the invention is particularly substantially independent of extended storage time even at 50° C., and of pH, and is tolerant of monovalent and multivalent salts in solution.

As an added feature of the invention, the residual VP monomer content of the polymers obtained herein is less than about 0.1% by weight. In aqueous based processes, in contrast, the formation of a gel mass during polymerization may trap considerable amounts of VP monomer in the polymeric gel network.

Examples of specific cosmetic formulations are presented as follows:

EXAMPLE 14

| Ingredients | Parts by Weight |
|---|---|
| CREAM RINSE | |
| Polymer of Ex. 1 | 2.0 |
| polyquaternium* 11 | 2.0 |
| etyl alcohol | 2.0 |
| emulsifying wax | 2.0 |
| citric acid | to pH 4 |
| deionized water | qs |
| fragrance | qs |
| preservative | qs |
| HAIR CONDITIONER | |
| Polymer of Ex. 1 | 4.0 |
| polyquaternium* 11 | 2.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid | to pH 4 |
| deionized water | qs |
| Germaben II | 1.00 |
| fragrance | qs |
| BLOW DRY STYLING LOTION | |
| Polymer of Ex. 1 | 1.5 |
| ethanol | 3.0 |
| polyquaternium* 11 | 2.0 |
| PEG-10 Castor oil | 0.2 |
| fragrance | 0.2 |
| phosphoric acid | to pH 6 |
| deionized water | qs |
| Germall 115 | 0.50 |
| CONDITIONING HAIR SPRAY | |
| Polymer of Ex. 2 | 2.0 |
| ethanol | 75.51 |

| Ingredients | Parts by Weight |
|---|---|
| ethyl ester of PVM/MA** copolymer | 4.0 |
| 2-amino-2-methyl-1-propanol 99% | 0.09 |
| fragrance | 0.2 |
| propellant | 20.0 |

*the quaternized ammonium polymer formed by reacting dimethyl sulfate and a copolymer of vinyl pyrrolidone and dimethylamino methylacrylate
**vinyl methyl ether/maleic anhydride

CONDITIONING SHAMPOO (1)

| Ingredients | Parts by Weight |
|---|---|
| Polymer of Ex. 3 | 1.5 |
| dodecylpyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |
| Germaben II | 0.50 |

CONDITIONING SHAMPOO (2)

| Ingredients | Parts by Weight |
|---|---|
| Polymer of Ex. 1 | 1.5 |
| polyquaternium 11 | 2.0 |
| sodium lauryl sulfate | 10.0 |
| sodium lauryl sulfate ether | 10.0 |
| Tego betain C | 10.0 |
| Kathon cg | 0.05 |
| deionized water | qs |

HAND AND BODY LOTION

| Ingredients | Parts by Weight |
|---|---|
| Polymer of Ex. 3 | 1.0 |
| preservative [Germaben IIE] | 1.0 |
| glyceryl stearate | 2.5 |
| cetyl alcohol | 3.0 |
| Alkamuls SMS | 2.5 |
| Alkamuls 20 | 2.5 |
| propyl paraben | 0.1 |
| deionized water | qs |

SUNSCREEN LOTION

| Ingredients | Parts by Weight |
|---|---|
| Polymer of Ex. 3 | 2.5 |
| sorbitol | 6.0 |
| preservative [Germaben IIE] | 1.0 |
| glyceryl stearate | 2.4 |
| stearic acid | 1.5 |
| octyl dimethyl PABA | 7.5 |
| benzophenone-3 | 2.5 |
| lanolin | 2.5 |
| deionized water | qs |

MOISTURIZING LOTION

| Ingredients | Parts by Weight |
|---|---|
| Polymer of Ex. 4 | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

BUBBLE BATH

| Ingredients | Parts by Weight |
|---|---|
| Polymer of Ex. 5 | 3.0 |
| ammonium nonoynol-4-sulfate | 30.0 |
| sodium cocoyl isothionate | 10.0 |
| cocamidopropyl hydroxysultaine | 10.0 |
| cocamide diethanolamide | 6.0 |
| sodium methyl cocyl taurate | 20.0 |
| aloe vera gel | 1.0 |
| coconut oil | 1.0 |
| glycol stearate | 1.0 |
| deionized water | qs |
| Germaben II | 0.50 |
| colorant | qs |

SHAMPOO FOR OILY HAIR

| Ingredients | Parts by Weight |
|---|---|
| Polymer of Ex. 5 | 3.0 |
| n-dodecylpyrrolidone | 1.0 |
| tetrasodium ethylenediamine tetra-acetic acid | 0.2 |
| sodium lauryl sulfate | 20.0 |
| alpha-olefin sulfonate | 20.0 |
| polyquaternium 11 | 0.5 |
| deionized water | qs |
| Germaben II | 0.50 |
| colorant | qs |
| fragrance | qs |
| added inorganic salts as desired for viscosity modification | |

SYNDET BAR (Superfatted)

| Ingredients | Parts by Weight |
|---|---|
| Polymer of Ex. 6 | 0.5 |
| stearic acid, triple pressed | 32.00 |
| kettle soap | 9.80 |
| sodiumcocoyl isethionate | 49.00 |
| sodium methyl cocoyl taurate | 6.90 |
| citric acid, 50% aqueous | 0.60 |
| titanium dioxide | 0.20 |
| fragrance | 1.00 |
| preservative | qs |

WATER RESISTANT EMOLLIENT AFTER SUN LOTION

| Ingredients | Parts by Weight |
|---|---|
| Polymer of Ex. 7 | 3.0 |
| mink Oil, Light Fraction | 11.00 |
| glyceryl stearate, self emulsifying | 1.00 |
| stearic acid | 2.50 |
| mineral oil and lanolin alcohol | 2.00 |
| myristyl myristate | 3.000 |
| mineral oil | 10.00 |
| PVP/Eicosene copolymer | 2.00 |
| triethanolamine | 0.70 |
| sorbitol | 3.00 |
| hydroxyethylcellulose | 0.30 |
| distilled water | qs |
| Germaben IIE | 1.00 |
| fragrance | qs |

NON-ALCOHOLIC CONDITIONING MOUSSE

| Ingredients | Parts by Weight |
|---|---|
| Polymer of Ex. 7 | 5.00 |
| polyquaternium 11 | 2.0 |
| Oleth-20 | 0.50 |
| fragrance | qs |
| deionized water | 77.50 |
| propellant A-46 | 15.00 |
| Germaben II | 0.50 |

SELF-HEATING AEROSOL SHAVING CREAM
(Used dual dispensing valve containing 30 ml stearic acid and 11% hydrogen peroxide)

| Ingredients | Parts by Weight |
|---|---|
| Polymer of Ex. 1 | 2.00 |
| stripped coconut fatty acid | 1.10 |
| sorbitol | 10.00 |
| stearic acid | 4.20 |
| PEG-40 soritan peroleate | 2.00 |
| triethanolamine | 3.00 |
| potassium hydroxide | 1.00 |
| potassium sulfite | 9.00 |
| fragrance | 0.80 |
| butyrated hydroxy toluene (BHT) | 0.01 |
| butyrated hydroxy anisole (BHA) | 0.01 |
| deionized water | qs |
| Germaben II | 0.50 |

CATIONIC MOUSSE HAND/BODY LOTION
(Used 85 Parts of the following formula to 15 parts propellant A-46)

| Ingredients | Parts by Weight |
|---|---|
| Polymer of Ex. 1 | 0.50 |
| polyquaternium 11 | 2.0 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |

AFTER SHAVE BALM

| Ingredients | Parts by Weight |
|---|---|
| Polymer of Ex. 1 | 1.00 |
| Carbomer 941 | 0.20 |

| Ingredients | Parts by Weight |
| --- | --- |
| tetrasodium ethylene diamine tetraacetic acid | 0.10 |
| cetearyl alcohol* and polyethylene glycol ether of cetearyl alcohol | 2.50 |
| isopropyl myristate | 1.00 |
| Oleth-20 | 1.00 |
| methyl gluceth 20 | 2.00 |
| triethanolamine, 98% | 0.20 |
| propylene glycol | 3.00 |
| SDA denatured alcohol | 7.50 |
| PVP/dimethylaminoethyl methacrylate | 7.00 |
| fragrance | 1.00 |
| distilled water | qs |
| preservative | qs |

*50/50 mixture of cetyl and stearyl alcohols

What is claimed is:

1. A cosmetic composition for the care of hair or skin consisting essentially of (1) about 0.2 to 10% by wt. of a strongly swellable, moderately crosslinked PVP polymer in the form of fine, white powders characterized by (a) an aqueous gel volume of about 15 to 150 ml/g of polymer, (b) a Brookfield viscosity in 5% aqueous solution of at least about 10,000 cps, and (c) being prepared directly by precipitation polymerization of VP in the presence of a crosslinking agent in the amount of about 0.2 to about 1% by weight of VP, (2) one or more active hair or skin care ingredients, and (3) a cosmetic vehicle selected from water, alcohol and mixtures thereof.

2. A cosmetic composition according to claim 1 wherein (a) is about 25 to 75 ml/g of polymer, (b) is at least about 15,000 cps, and (c) is about 0.25 to 0.8%.

3. A cosmetic composition according to claim 1 wherein (a) is about 30 to 60 ml/g of polymer; (b) is about 20,000 to 50,000 cps; and (c) is about 0.35 to 0.6%.

4. A cosmetic composition according to claim 1 wherein said precipitation polymerization is carried out in an organic solvent.

5. A cosmetic composition according to claim 1 in which said crosslinking agent is selected from N,N'-divinylimidazolidone, pentaerythritol triallyl ether, triallyl-1,3,5-triazine-2,4,6(1H,3H,5H)-trione and 2,4,6-triallyloxy-1,3,5-triazine.

6. A cosmetic composition according to claim 1 which contains about 0.5 to 5% by wt. of said polymer.

7. A cosmetic composition according to claim 1 wherein the cosmetic formulation is a shampoo and the amount of crosslinked polyvinylpyrrolidone is effective for conditioning hair.

8. A cosmetic formulation of claim 1 wherein (2) is a surfactant selected from an alkali metal lauryl sulfate, an alkali metal lauryl sulfate ether, ammonium lauryl sulfate and an α-olefin sulfonate.

* * * * *